United States Patent [19]

Ogiu

[11] 4,419,987

[45] Dec. 13, 1983

[54] LASER ENDOSCOPE

[75] Inventor: Hisao Ogiu, Oume, Japan

[73] Assignee: Olympus Optical Co., Ltd., Tokyo, Japan

[21] Appl. No.: 214,095

[22] Filed: Dec. 8, 1980

[30] Foreign Application Priority Data

Dec. 21, 1979 [JP] Japan .................. 54-166433

[51] Int. Cl.³ .............................................. A61B 1/00
[52] U.S. Cl. ............................................ 128/4; 128/6
[58] Field of Search ................... 128/4, 6; 220/288

[56] References Cited

U.S. PATENT DOCUMENTS

| 3,858,577 | 1/1975 | Bass et al. |
| 3,896,793 | 7/1975 | Mitsui et al. ................. 128/6 |
| 3,937,324 | 2/1976 | Whiteford ................. 220/288 |
| 4,273,109 | 6/1981 | Enderby ................. 128/6 |
| 4,279,486 | 7/1981 | Ogawa ................. 128/6 |

FOREIGN PATENT DOCUMENTS

| 53-84379 | 7/1978 | Japan . |
| 2041559 | 9/1980 | United Kingdom ............ 128/6 |

Primary Examiner—Kyle L. Howell
Assistant Examiner—Max F. Hindenburg
Attorney, Agent, or Firm—Frishauf, Holtz, Goodman & Woodward

[57] ABSTRACT

A laser endoscope has a distal end portion detachably fitted with a holder which can cover the distal end of a channel extending through the laser endoscope body in a liquid-tight state and whose distal end holds a glass cover. The detachable attachment of the holder to the distal end portion of the laser endoscope enables a single channel to be concurrently used not only as a laser guide channel but also as a forceps channel.

1 Claim, 8 Drawing Figures

LASER ENDOSCOPE

BACKGROUND OF THE INVENTION

This invention relates to a laser endoscope wherein a forceps channel is concurrently applicable as a laser guide channel.

An endoscope is generally provided with a channel through which a forceps is inserted into an endoscope body. This forceps channel is opened at the distal end of the endoscope body. The forceps is pushed through the opening into the coeliac cavity of a human body to sample a coeliac tissue for a biopsy.

In recent years, an affected coeliac part is medically treated by the process of inserting a laser guide through a channel formed in an endoscope body and irradiating laser beams on the affected coeliac cavity through the laser guide. In this case, the laser guide opening is closed with a glass cover to prevent the laser guide from being soiled with coeliac fluid.

When a laser guide is inserted into a forceps channel extending through an endoscope using a forceps, the distal end of the laser guide body tends to be soiled, for example, with coeliac fluid, obstructing the irradiation of laser beams on an affected coeliac part, while a forceps cannot be put into the coeliac cavity through at laser guide channel of a laser endoscope whose distal end is closed with a glass cover. Hitherto, therefore, a separate exclusive type of endoscope has had to be provided, when a biopsy is undertaken by the above-mentioned application of a forceps or similar instrument or an affected coeliac part is medically treated by applying laser beams. Such circumstance involves increased cost and inconvenience.

It is accordingly the object of this invention to provide a laser type endoscope wherein a glass cover is detachably attached to a distal end opening of a forceps channel, and the forceps channel is concurrently used to allow for the insertion of a laser guide.

SUMMARY OF THE INVENTION

To attain the above-mentioned object, this invention provides a laser endoscope which comprises an endoscope body, a channel extending through the endoscope body and a glass cover holder detachably attached to a distal end of the channel and holding a glass cover. When fitted with the glass cover holder, the channel is sealed in a liquid-tight state for use as a laser guide channel, and, when released from the glass cover holder, is applied for insertion of a forceps. Therefore, a laser endoscope embodying this invention allows for the application of a forceps without broadening the diameter.

DETAILED DESCRIPTION

Figure 1:
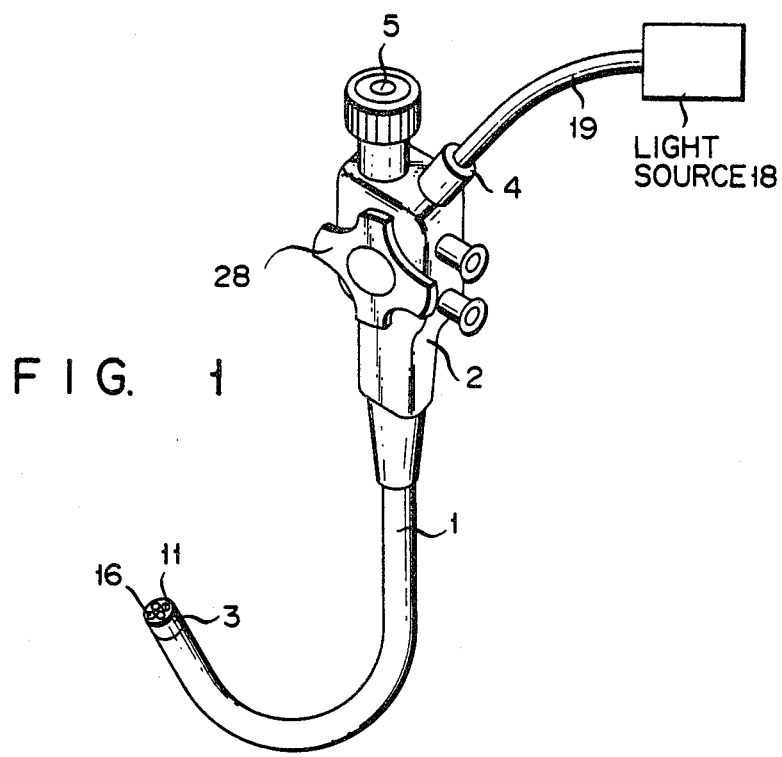
FIG. 1 is an oblique whole view of a laser endoscope according to one embodiment of this invention.
Figure 2:
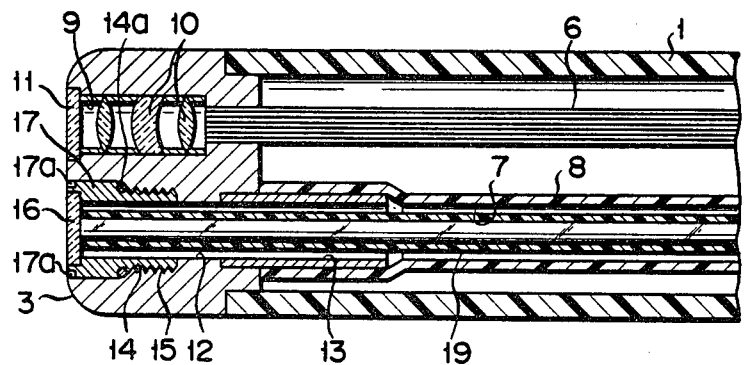
FIG. 2 is a longitudinal cross sectional view of a distal end portion of the laser endoscope according to the embodiment of FIG. 1.
Figure 3:
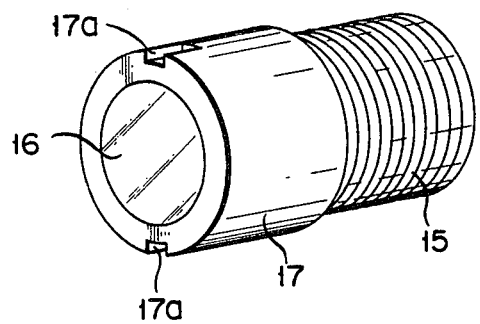
FIG. 3 is an oblique view of a glass cover holder used in FIG. 2.

Referring to FIGS. 1 to 3, a control section 2 is provided at a proximal end of an endoscope body 1 comprising a flexible tube. A cylindrical distal end portion 3 is provided on the distal end of the endoscope body 1. The control section 2 is provided with a forceps inlet 4 and and eyepiece assembly 5. There extends through the endoscope body 1 an image guide 6 formed of an optical fiber bundle, one end of which is optically connected to the eyepiece assembly 5, and a guide tube 8 which is prepared from tetrafluoroethylene, one end of which communicates with the forceps inlet 4 and whose interior is concurrently used as a channel 7. The other end of the image guide 6 is inserted into a first axial hole 9 provided in the cylindrical distal end portion 3. Held in the first axial hole 9 is an objective 10 optically connected to the other end of the image guide 6 and an objective glass cover 11. A second axial hole 12 is also formed in the distal end portion 3 to be used as part of the channel 7. The other end of the guide tube 8 is securely set in a shorter tube 13 fitted into the rear end portion of the second axial hole 12. Internal screw threads 14 are formed in the inner peripheral wall of the second axial hole 12.

Engaged with the internal screw threads 14 are external screw threads 15 formed on the outer peripheral wall of a hollow cylindrical holder 17 whose distal end sealingly holds a disc-shaped glass cover 16. The holder 17 is detachably set in the second axial hole 12 in a state rendered liquid-tight by means of an O-ring 14a disposed between the holder 17 and second axial hole 12. As best shown in FIG. 3, a pair of diametrically facing notches 17a are cut out in the front outer peripheral edge of the holder 17. The holder 17 is detachably inserted into the second axial hole 12 by means of a tool having a pair of pawls inserted into the second axial hole 12.

A laser guide 19 whose rear end is connected to a laser source 18 (FIG. 1) disposed externally of the endoscope is inserted into the channel 7 through the forceps inlet 4 formed in the control section 2. The distal end of the laser guide 19 is pressed against the inner wall of the glass cover 16.

With a laser endoscope embodying this invention which is arranged as described above, the holder 17 sealingly holding the disc-shaped glass cover 16 is detachably fitted into the second axial hole 12 formed in the distal end portion 3 for communication with the channel 7. The glass cover 16 closes the distal end opening of the second axial hole 12 or the channel 7. When, therefore, the endoscope body 1 is inserted into the coeliac cavity with the laser guide 19 inserted into the channel 7, the laser guide 19 is prevented from being soiled by the deposition of, for example, a coeliac fluid. As a result, laser beams emitted from the laser source 18 through the laser guide 19 are unfailingly irradiated on an affected coeliac part to ensure its medical treatment.

When the holder 17 is taken out of the second axial hole 12 before a forceps is inserted into the channel 7 for biopsy, the channel 7 is left open, enabling the forceps to be pushed into the coeliac cavity through the channel 7 and second axial hole 12. In other words a single channel can be concurrently used for insertion of a laser guide when the holder 17 is fitted as well as for insertion of a forceps when the holder 17 is taken off.

Figure 4:
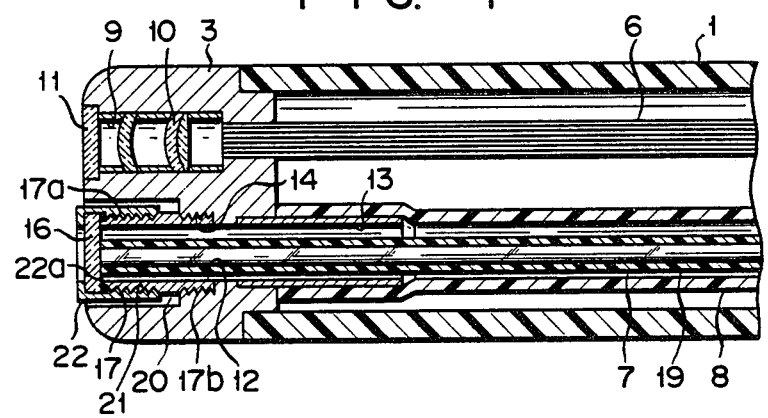
FIG. 4 is a longitudinal cross sectional view of a main part of a laser endoscope according to another embodiment of the invention.
Figure 5:
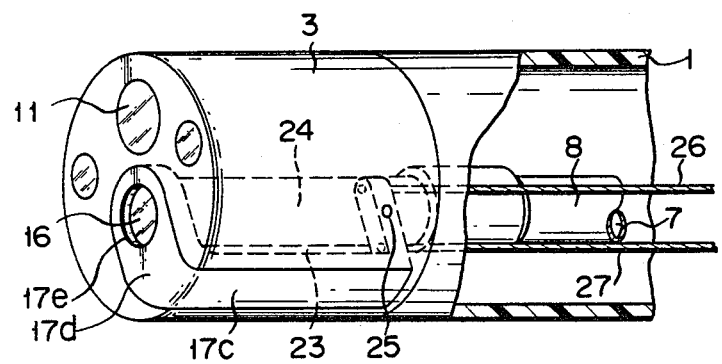
FIG. 5 is an oblique view of a main part of a laser endoscope according to still another embodiment of the invention.

Description is now given with reference to FIG. 4 of a laser endoscope according to a second embodiment of this invention. An annular groove 20 (or a cylindrical cavity having larger diameter than that of the later described cap 22) is formed in the forward inner peripheral wall of the second axial hole 12 of the distal end portion 3. External screw threads 17b are formed on the rear outer peripheral wall of a hollow cylindrical holder 17 for engagement with internal screw threads 14 formed in the rear end portion of the second axial hole 12. The holder 17 is detachably fitted to the distal end portion 3 in a light-tight state. The external screw threads 17b formed on the rear outer peripheral wall of the holder 17 are also engaged with internal screw threads 21 formed in the inner peripheral wall of a ring-shaped cap 22. A packing 22a is provided between the holder 17 and cap 22 to seal a space defined therebetween. A disc-shaped glass cover 16 is fitted between the front end of the holder 17 and the front inner wall of the cap 22. When the holder 17 is fitted to the distal end portion 3, the cap 22 projects from the front end face of the distal end portion 3. The holder 17 can be removed from the distal end portion 3 either by gripping the projecting portion of the cap 22 with the fingers or by, as in the embodiment of FIG. 2, using a tool having a pair of pawls engageable with a pair of diametrically facing notches cut out in the front outer peripheral wall of the cap 22. The insertion of the holder 17 into the distal end portion 3 is carried out in the same manner as described above. In use, the annular groove 20 is concentric with the cap 22.

Description is now given with reference to FIGS. 5 to 8 of a laser endoscope according a third embodiment of the invention. A holder-receiving space 23 having a U-shaped cross section is formed in the distal end portion in a state extending axially thereof. Through the space 23 extends a shorter tube 24 constituting part of the channel 7.

The holder 17 comprises a plate-like main portion 17c fully covering that portion of the holder-receiving space 23 which is opened on the lateral side of the distal end portion 3. A rising portion 17d extends substantially at right angles from the front end of the main portion 17c. A circular hole 17e fitted with the disc-shaped glass cover 16 is formed in the rising portion 17d. When the holder 17 is used, the rising portion 17d sets the glass cover 16 at the front end of the shorter tube 24 concentrically therewith. A pair of arms 17f extends from both the rear lateral ends of the main portion 17c in parallel with the rising portion 17d and in the same direction as that in which the rising portion 17d extends. An intermediate part of the respective arms 17f is penetrated at right angles by a shaft 25, both ends of which are fixed to the distal end portion 3. First and second control wires 26, 27 are fixed at their one end to the rear side of the corresponding arms 17f, with the shaft 25 interposed between both wires 26, 27. The second wire 27 extends along that side of the shaft 25 which faces the main portion 17c. The first wire 26 extends along the opposite side of the shaft 25. The control wires 26, 27 extend through the endoscope body 1 and are connected at the other end to a wire-operating mechanism (not shown) set in the control section 2. The wire-operating mechanism is interlockingly actuated with a knob 28 (FIG. 1) provided on one lateral side of the control section 2. The control wires 26, 27 reciprocate through the endoscope body 1 by the operation of the knob 28.

Figure 6:
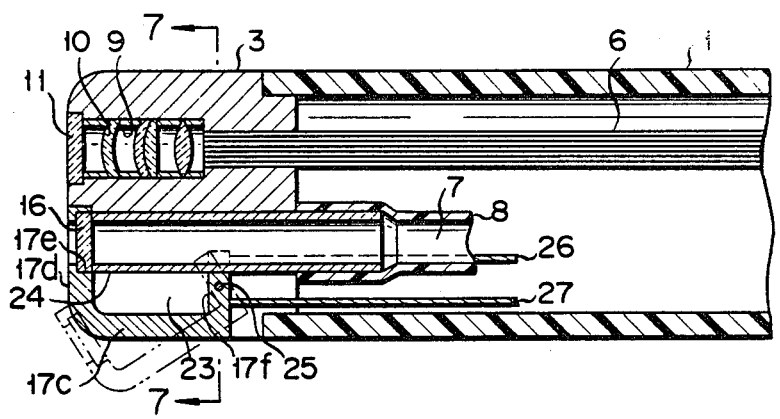
FIG. 6 is a longitudinal cross sectional view of FIG. 5.
Figure 7:
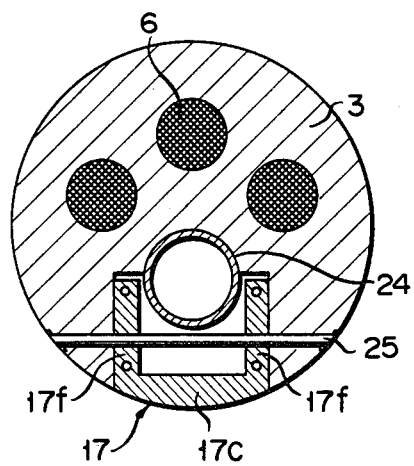
FIG. 7 is a transverse cross sectional view on line 7—7 of FIG. 6.
Figure 8:
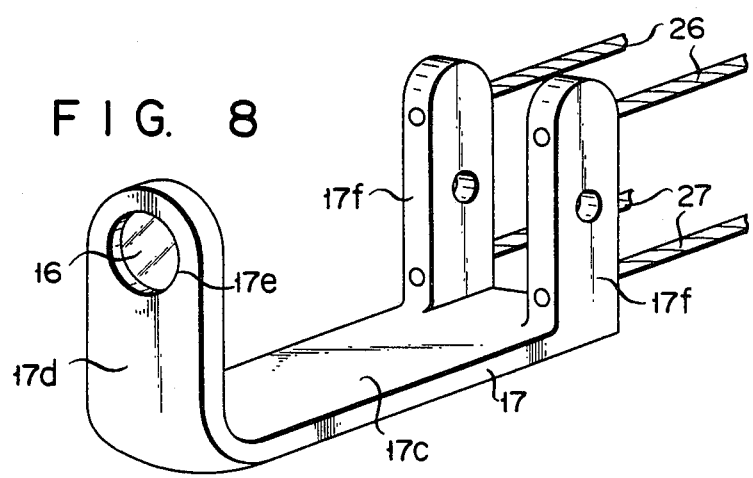
FIG. 8 is an oblique view of a holder used in FIG. 5.

When, with a laser endoscope according to the third embodiment of FIGS. 5 to 8, the knob 28 causes the first control wire 26 extending along a line close to the free end of the corresponding arm 17f as viewed from the shaft 25 acting as the rotation fulcrum of the holder 17 to be loosened and the second control wire 27 extending along a line close to the main portion 17c as viewed from the shaft 25 to be pulled, the holder 17 is shifted to a position indicated in chain lines in FIG. 6. As a result, the glass cover 16 supported by the holder 17 is displaced from the distal end of the shorter tube 24, namely, that of the channel 7, thereby allowing the channel 7 to be used as a forceps channel. Conversely, where the first control wire 26 is pulled and the second control wire 27 is loosened, the holder 17 is rotated in the opposite direction to the preceding case, causing the distal end of the shorter tube 24 or the channel 7 to be closed by the glass cover 16, thereby allowing the channel 7 to be used as a laser guide channel. The above-mentioned arrangement enables the channel 7 to be selectively used as a passage of forceps, or laser guide 19 as need arises by properly operating the first and second control wires 26, 27.

The parts of the third embodiment the same as those of the first and second embodiments are denoted by the same numerals, description thereof being omitted.

In every embodiment, the glass cover is disposed in the holder in a liquid-tight state.

What is claimed is:
1. A laser endoscope comprising:
   an endoscope body having two ends;
   a distal end portion fixed to one end of the endoscope body, the distal end portion having internal screw threads formed therein:
   a control section fixed to the other end of the endoscope body;
   a channel extending through the distal end portion, endoscope body and control section and having a distal end;
   a holder which is detachably attached in the distal end portion, and, when attached in the distal end portion, covers the distal end of the channel in a liquid-tight state; and
   a glass cover which is so disposed in the holder so as to face the distal end of the channel when said holder is put to use by being attached to the distal end portion;
   said holder comprising a hollow cylindrical member having two ends, one end of which is fitted with the glass cover, and the other end of which is provided with external screw threads for engagement with the internal screw threads in the distal end portion; and
   said holder further comprising notches formed at the end thereof which is fitted with the glass cover to provide means for gripping the holder so that it can be rotated to disengage from the internal screw threads in the distal end portion.

* * * * *